(12) United States Patent
Matsumura et al.

(10) Patent No.: US 11,931,479 B2
(45) Date of Patent: Mar. 19, 2024

(54) ARTIFICIAL BLOOD VESSEL

(71) Applicant: GUNZE LIMITED, Ayabe (JP)

(72) Inventors: Goki Matsumura, Tokyo (JP); Hideki Sato, Kyoto (JP); Mieko Ishikawa, Kyoto (JP)

(73) Assignee: GUNZE LIMITED, Kyoto (JP)

( * ) Notice: Subject to any disclaimer, the term of this patent is extended or adjusted under 35 U.S.C. 154(b) by 742 days.

(21) Appl. No.: 17/064,082

(22) Filed: Oct. 6, 2020

(65) Prior Publication Data
US 2021/0128788 A1    May 6, 2021

(30) Foreign Application Priority Data

Nov. 5, 2019 (JP) ................................. 2019-200733

(51) Int. Cl.
*A61L 27/50* (2006.01)
*A61L 27/18* (2006.01)
(Continued)

(52) U.S. Cl.
CPC ............. *A61L 27/507* (2013.01); *A61L 27/18* (2013.01); *A61L 27/56* (2013.01); *A61L 27/58* (2013.01);
(Continued)

(58) Field of Classification Search
CPC ........ A61L 27/507; A61L 27/18; A61L 27/56; A61L 27/58; D02G 3/045; D02G 3/38;
(Continued)

(56) References Cited

U.S. PATENT DOCUMENTS

| 5,891,558 A * | 4/1999 | Bell ........................ A61L 27/60 |
| | | 428/305.5 |
| 2005/0113938 A1* | 5/2005 | Jamiolkowski ....... A61L 27/446 |
| | | 623/23.74 |

FOREIGN PATENT DOCUMENTS

| JP | 2001-078750 | 3/2001 |
| JP | 2007-130179 | 5/2007 |
| JP | 2009-160079 | 7/2009 |

OTHER PUBLICATIONS

Cooper, et al., "In vivo optimization of a living dermal substitute employing cultured human fibroblasts on a biodegradable polyglycolic acid or polyglactin mesh", Biomaterials, vol. 12, Mar. 1991, pp. 243-248.

(Continued)

*Primary Examiner* — Yashita Sharma
(74) *Attorney, Agent, or Firm* — HSML, P.C.

(57) ABSTRACT

The present invention provides an artificial blood vessel that can achieve a balance between cell penetration efficiency and crush resistance and can regenerate a blood vessel at very high efficiency. Provided is an artificial blood vessel having a tubular shape, including: a foam containing a bioabsorbable material; a reinforcement A containing a bioabsorbable material; and a reinforcement B including threads containing a bioabsorbable material, the foam being reinforced with the reinforcements A and B, wherein the reinforcement A is a non-woven fabric, a film, or a weft-knitted, warp-knitted, or woven fabric made of knitted or woven fibers, the reinforcement B includes monofilament threads each having a cross-sectional diameter of 0.1 mm or more and 1 mm or less, the reinforcement B includes a winding portion having a helical shape, a ring shape, or an X shape and a warp thread portion stretched in a direction parallel to a longitudinal direction of the artificial blood vessel, and the artificial blood vessel is a composite includ- (Continued)

ing the reinforcement A and reinforcement B inside the foam.

2 Claims, 2 Drawing Sheets

(51) Int. Cl.
    *A61L 27/56*      (2006.01)
    *A61L 27/58*      (2006.01)
    *D02G 3/04*      (2006.01)
    *D02G 3/38*      (2006.01)
    *D02G 3/44*      (2006.01)

(52) U.S. Cl.
    CPC ............... *D02G 3/045* (2013.01); *D02G 3/38* (2013.01); *D02G 3/448* (2013.01)

(58) Field of Classification Search
    CPC ...... D02G 3/448; D10B 2509/06; A61C 8/00; A61F 2/02
    See application file for complete search history.

(56) References Cited

OTHER PUBLICATIONS

Vacanti, et al., "Synthetic Polymers Seeded with Chondrocytes Provide a Template for New Cartilage Formation", Plastics and Reconstructive Surgery, vol. 88, No. 5, Nov. 1991, pp. 753-759.

\* cited by examiner (a)

(b)

ARTIFICIAL BLOOD VESSEL

TECHNICAL FIELD

The present invention relates to an artificial blood vessel that can achieve a balance between cell penetration efficiency and crush resistance and can regenerate a blood vessel at very high efficiency.

BACKGROUND ART

Artificial blood vessels that are currently most frequently used in clinic are those containing non-absorbable polymers, such as GORE-TEX. Such artificial blood vessels can exhibit very similar physical properties to those of blood vessels, and have achieved some success in short-term vascular reconstruction. Unfortunately, artificial blood vessels containing non-absorbable polymers remain in the body as foreign matter for a long time after implantation, and thus require continuous administration of anti-coagulants and the like. In addition, when artificial blood vessels are used in infants, repeat surgery is required as they grow older.

To overcome the situation, tissue regeneration by what is called regenerative medicine has been attempted. The regenerative medicine, in a broad sense, is a form of medicine that involves transplanting cells or a device or the like incorporating cells therein into a patient's body to regenerate a damaged organ or tissue and thereby restore lost body functions.

For regenerative medicine, many studies have been reported on various tissues, including skin (Non-Patent Literature 1) and cartilage (Non-Patent Literature 2).

To apply regenerative medicine to vascular regeneration, the present inventors developed a vascular regeneration substrate including a bioabsorbable polymer foam and a bioabsorbable polymer reinforcement incorporated as a core in the foam (Patent Literature 1). In this vascular regeneration substrate, the foam serves as a scaffold to which penetrating cells can firmly adhere, whereas the reinforcement functions to withstand blood flow and maintain strength until the blood vessel is regenerated after implantation, or functions as a reinforcement to withstand suturing. The foam and reinforcement both contain a bioabsorbable polymer, so that the material is absorbed after regeneration of the blood vessel, eliminating the need for the continuous use of anti-coagulants and the like. In addition, the regenerated blood vessel is expected to grow because it is autologous tissue.

The success of vascular tissue regeneration in artificial blood vessel implantation is dependent on the ease of cell penetration into the artificial blood vessel and on the absence of stenosis before the regeneration of vascular tissue. For easy cell penetration, the material of the artificial blood vessel is required to be flexible and highly water-absorbing. On the other hand, the artificial blood vessel is required to have mechanical strength enough to prevent the tubular shape from crushing, because proliferated cells in the tissue regeneration process exhibit tensile force in the lumen direction and thus cause stenosis. In other words, the artificial blood vessel is required to exhibit high compressive elastic modulus to maintain its bore when the tube is compressed. There is a trade-off relationship between being flexible and highly water-absorbing and having high compressive elastic modulus, and it is difficult to achieve a balance therebetween. In addition, an artificial blood vessel having high compressive elastic modulus for a long time is more likely to cause hardening of the regenerated blood vessel called "calcification".

CITATION LIST

Patent Literature
Patent Literature 1: JP 2001-78750 A
Non-Patent Literature
Non-Patent Literature 1: ML. Cooper, L. F. Hansbrough, R. L. Spielvogel et al, Biomaterials, 12:243-248, 1991
Non-Patent Literature 2: C. A. Vacanti, R. langer, et al, Plast. Reconstr. Surg, 88:753-759, 1991

SUMMARY OF INVENTION

Technical Problem

To overcome the situation, there have been proposed tubular artificial blood vessels in which a foam containing a bioabsorbable material is reinforced with a reinforcement containing a bioabsorbable material and a reinforcing thread containing a bioabsorbable material. An artificial blood vessel with such a structure can achieve a balance between high water absorbency and crush resistance. However, since artificial blood vessels may be used in vital organs such as cardiac blood vessels, there is a demand for an artificial blood vessel more resistant to crush to improve safety.

The present invention aims to provide an artificial blood vessel that can achieve a balance between cell penetration efficiency and crush resistance and can regenerate a blood vessel at very high efficiency.

Solution to Problem

The present invention relates to an artificial blood vessel having a tubular shape, including: a foam containing a bioabsorbable material; a reinforcement A containing a bioabsorbable material; and a reinforcement B including threads containing a bioabsorbable material, the foam being reinforced with the reinforcements A and B, wherein the reinforcement A is a non-woven fabric, a film, or a weft-knitted, warp-knitted, or woven fabric made of knitted or woven fibers, the reinforcement B includes monofilament threads each having a cross-sectional diameter of 0.1 mm or more and 1 mm or less, the reinforcement B includes a winding portion having a helical shape, a ring shape, or an X shape and a warp thread portion stretched in a direction parallel to a longitudinal direction of the artificial blood vessel, and the artificial blood vessel is a composite including the reinforcement A and reinforcement B inside the foam.

The present invention is described in detail below.

The present inventors made intensive studies. The substrate has been considered to require flexibility, but the inventors found out that, surprisingly, purposefully reducing flexibility in the longitudinal direction of the substrate increases crush resistance, leading to higher blood vessel regeneration efficiency. The inventors thus completed the present invention.

The artificial blood vessel of the present invention is an artificial blood vessel having a tubular shape and including a foam containing a bioabsorbable material, a reinforcement A containing a bioabsorbable material, and a reinforcement B including threads containing a bioabsorbable material, the foam being reinforced with the reinforcements A and B.

In such a configuration, the foam can serve as a scaffold to which penetrating cells can firmly adhere, while the reinforcements A and B can withstand blood flow to maintain strength until the blood vessel is regenerated after implantation. The foam and reinforcements A and B both contain a bioabsorbable polymer, so that the material is absorbed after regeneration of the blood vessel, eliminating the need for the continuous use of anti-coagulants and the like. In addition, the regenerated blood vessel is expected to grow because it is autologous tissue.

The artificial blood vessel of the present invention is a composite including the reinforcement A and reinforcement B inside the foam.

Such a structure allows the reinforcements A and B to sufficiently function to maintain strength, and also allows regeneration to progress from the inside of the blood vessel, leading to early blood vessel regeneration. In particular, the reinforcements A and B are preferably positioned at the center in the thickness direction of the foam. In other words, the reinforcements A and B are preferably positioned at the center of the tube that is the artificial blood vessel of the present invention. The composite herein refers to one in which the reinforcements A and B and the foam are integrated together and not easily separable from each other.

Examples of the bioabsorbable material constituting the foam includes polyglycolide, polylactide (D, L, or DL), polycaprolactone, glycolide-lactide (D, L, or DL) copolymers, glycolide-ε-caprolactone copolymers, lactide (D, L, or DL)-ε-caprolactone copolymers, poly(p-dioxanone), and glycolide-lactide (D, L, or DL)-ε-caprolactone copolymers. These may be used alone or in combination of two or more thereof.

The foam preferably contains a lactide (D, L, or DL)-ε-caprolactone copolymer having a lactide (D, L, or DL) content of 50 to 54 mol % and a ε-caprolactone content of 50 to 46 mol %.

Use of a lactide (D, L, or DL)-ε-caprolactone copolymer with such a component ratio allows the artificial blood vessel to have flexibility and water absorbency to ensure penetration of sufficient number of cells while having high compressive elastic modulus to reduce the occurrence of stenosis. The lactide (D, L, or DL) content of 50 mol % or more (ε-caprolactone content of less than 50 mol %) can provide high compressive elastic modulus when the tube is compressed, further reducing the occurrence of stenosis. The lactide (D, L, or DL) content of 54 mol % or less (ε-caprolactone content of more than 46 mol %) can provide high flexibility and thus high water absorbency, facilitating penetration of cells.

Herein, regarding the component ratio of the lactide (D, L, or DL)-ε-caprolactone copolymer, only one copolymer may be used and the component ratio of the copolymer may satisfy the above range of the ratio. Alternatively, two or more copolymers having different component ratios may be used in combination, and the component ratio of the two or more copolymers as a whole may satisfy the above range of the ratio.

The foam may be subjected to hydrophilization treatment. The hydrophilized foam can quickly absorb cell suspension when brought into contact therewith, and thus allows more efficient and uniform cell penetration.

Any hydrophilization treatment may be performed. Examples thereof include plasma treatment, glow discharge treatment, corona discharge treatment, ozone treatment, surface graft treatment, and UV irradiation treatment. Preferred among these is plasma treatment because it significantly increases the water absorbency without changing the appearance of the artificial blood vessel.

The foam needs to have a pore size that allows appropriate adhesion and proliferation of penetrating cells while hardly causing blood leakage even when the artificial blood vessel is implanted to cardiovascular tissue. Specifically, the lower limit of the pore size is preferably 5 μm and the upper limit thereof is preferably 100 μm. The foam having a pore size of 5 μm or more allows cells to easily penetrate into the pores of the foam. The foam having a pore size of 100 μm or less is less likely to cause blood leakage when the artificial blood vessel is implanted. The lower limit of the pore size of the foam is more preferably 10 μm and the upper limit thereof is more preferably 50 μm.

The average pore size of the fine pores can be measured by a conventionally known method such as mercury porosimetry or image analysis.

Preferably, the lower limit of the thickness of the foam is 0.2 mm and the upper limit thereof is 3.0 mm.

Use of a foam having such a thickness allows the artificial blood vessel to have flexibility and water absorbency to ensure penetration of sufficient number of cells while having high compressive elastic modulus to reduce the occurrence of stenosis. The foam having a thickness of 0.2 mm or more can provide a high compressive elastic modulus and thus reduce the occurrence of stenosis. The foam having a thickness of 3.0 mm or less can provide high flexibility and thus high water absorbency, facilitating penetration of cells. The lower limit of the thickness of the foam is more preferably 0.4 mm and the upper limit thereof is more preferably 1.2 mm.

The method for adjusting the thickness of the foam is not limited. For example, in producing the artificial blood vessel of the present invention by the later-described production method, the thickness may be adjusted by adjusting the concentration and amount of the solution of the bioabsorbable material for forming the foam.

The reinforcement A is a non-woven fabric, a film, or a weft-knitted, warp-knitted, or woven fabric made of knitted or woven fibers.

The reinforcement having any of the forms can sufficiently function as a reinforcement.

The reinforcement A preferably contains at least one selected from the group consisting of polyglycolide, polylactide (D, L, or DL), polycaprolactone, a glycolic acid-lactide (D, L, or DL) copolymer, a glycolic acid-ε-caprolactone copolymer, a lactide (D, L, or DL)-ε-caprolactone copolymer, and poly(p-dioxanone).

The reinforcement A preferably contains bioabsorbable fibers coated with a bioabsorbable material. Use of such bioabsorbable fibers coated with a bioabsorbable material makes it possible to achieve a balance between the flexibility and water absorbency and the high compressive elastic modulus that prevents stenosis when the tube is compressed.

The bioabsorbable fibers coated with a bioabsorbable material are not limited. For example, polyclycolide fibers coated with a lactide (D, L, or DL)-ε-caprolactone copolymer are suitable.

The coating method is not limited. Examples thereof include: a method in which polyglycolide fibers are immersed in a lactide (D, L, or DL)-ε-caprolactone copolymer solution, taken out of the solution, dried, and then formed into the reinforcement; and a method in which the reinforcement is formed using polyglycolide fibers, then immersed in a lactide (D, L, or DL)-ε-caprolactone copolymer solution, taken out of the solution, and dried.

The reinforcement A preferably includes twisted threads obtained by twisting bioabsorbable multifilament threads. Use of such twisted threads allows the artificial blood vessel to have flexibility and water absorbency while having high compressive elastic modulus to reduce the occurrence of stenosis.

The twisted threads preferably have an S twist at 350 T/m or more or a Z twist at 220 T/m or more.

The reinforcement B includes a winding portion having a helical shape, a ring shape, or an X shape.

The reinforcement B having the winding portion and the later-described warp thread portion can make the resulting artificial blood vessel more resistant to crush, and also can improve the blood vessel regeneration efficiency. In particular, to achieve higher compressive elastic modulus and higher blood vessel regeneration efficiency, the reinforcement B preferably has a helical shape, more preferably the shape of a pair of helices combined to have opposite winding directions.

For a winding portion having a helical shape or a ring shape, the lower limit of the winding pitch of the winding portion is preferably 1 mm and the upper limit thereof is preferably 10 mm. The winding portion having a winding pitch of 1 mm or more can reduce calcification to further improve the blood vessel regeneration efficiency. The winding portion having a winding pitch of 10 mm or less can further increase the reinforcing effect. The lower limit of the winding pitch of the winding portion is more preferably 2 mm and the upper limit thereof is more preferably 8 mm.

The reinforcement B includes a warp thread portion stretched in a direction parallel to the longitudinal direction of the artificial blood vessel.

Since actual blood vessels expand and contract, a certain degree of elasticity in the longitudinal direction of the artificial blood vessel, namely the direction in which the tube expands, has been considered to improve the blood vessel regeneration efficiency. However, the present inventors found out that an artificial blood vessel having elasticity in the longitudinal direction is susceptible to stenosis, and thus reduces the blood vessel regeneration efficiency. In the present invention, the warp thread portion restricts expansion and contraction of the substrate in the longitudinal direction, so that stenosis is less likely to occur than in conventional artificial blood vessels, resulting in improved blood vessel regeneration efficiency. The reinforcement B may contain only one warp thread portion or two or more warp thread portions. To further reduce expansion and contraction of the substrate in the longitudinal direction, the reinforcement B preferably includes two or more warp thread portions.

As used herein, "stretched in a direction parallel to the longitudinal direction" means that there is no slack in the warp thread portion when no force is applied to the substrate, and the direction in which the warp thread portion extends is parallel to the longitudinal direction of the substrate. Even if the warp thread portion is not linear because, for example, it is tied to another portion, the warp thread portion is within the scope of the present invention as long as there is no slack in the warp thread portion and the direction in which the warp thread portion as a whole extends is parallel to the longitudinal direction of the substrate.

The reinforcement B may have any structure as long as it includes the winding portion and the warp thread portion. The winding portion and warp thread portion may be present independently of each other, or the warp thread portion may be tied to the winding portion. In particular, to reduce expansion and contraction of the substrate in the longitudinal direction to improve the blood vessel regeneration efficiency, the warp thread portion is preferably tied to the winding portion. Preferably, the winding portion includes a pair of helical threads containing a bioabsorbable material and combined to have opposite winding directions, and an intersection of the threads is tied with a thread constituting the warp thread portion.

FIG. 1 schematically shows exemplary structures of the reinforcement B in the present invention. FIG. 1(a) shows a structure in which a winding portion has a helical shape and warp thread portions are tied to the winding portion. FIG. 1(b) shows a structure in which a winding portion includes a pair of helical threads containing a bioabsorbable material and combined to have opposite winding directions, and intersections of the threads are tied with threads constituting warp thread portions.

As shown in FIG. 1(a), a reinforcement B 1 includes a winding portion 11. The winding portion 11 includes a thread containing a bioabsorbable material and wound in the circumferential direction of the artificial blood vessel. The reinforcement B 1 functions to reduce stenosis of the artificial blood vessel. The reinforcement B 1 also includes warp portions 12 stretched in a direction parallel to the longitudinal direction of the substrate. These warp thread portions 12 reduce expansion and contraction, especially expansion, of the substrate in the longitudinal direction, thus further reducing the occurrence of stenosis. This can further increase the blood vessel regeneration efficiency. Tying the warp thread portions 12 to the winding portion 11 can further reduce expansion and contraction of the substrate in the longitudinal direction.

The reinforcement B more preferably has a structure as shown in FIG. 1(b). In the structure of FIG. 1(b), the winding portion 11 includes a pair of helical threads combined to have opposite winding directions, and the warp thread portions 12 tie the intersections on the paths of the warp thread portions 12. Such a structure can further reduce expansion and contraction of the resulting artificial blood vessel in the longitudinal direction, and thus can further reduce the occurrence of stenosis to further improve the blood vessel regeneration efficiency. Although the intersections of the threads in FIG. 1(b) are tied by wrapping the warp thread portions around them once, the intersections may be tied by any method.

The threads containing a bioabsorbable material to constitute the reinforcement B preferably contain at least one selected from the group consisting of poly-L-lactide, a lactide (D, L, or DL)-ε-caprolactone copolymer, and a glycolic acid-ε-caprolactone copolymer, more preferably contain a lactide (D, L, or DL)-ε-caprolactone copolymer. The reinforcing threads containing a lactide (D, L, or DL)-ε-caprolactone copolymer can maintain sufficient strength for a while after implantation, thus preventing the artificial blood vessel from crushing and causing stenosis. Yet, by the time the blood vessel is regenerated to some extent, the reinforcing threads have lost its strength through decomposition and absorption. In addition, the material does not remain, preventing decomposition of minerals and thus efficiently preventing calcification.

Regarding the component ratio when the threads containing a bioabsorbable material contain a lactide (D, L, or DL)-ε-caprolactone copolymer, the lactide (D, L, or DL):ε-caprolactone ratio (molar ratio) is preferably 90:10 to 45:55. With a lactide (D, L, or DL) ratio of 90 or less, the reinforcing threads have more appropriate hardness and decomposition rate, and thus can further improve the blood vessel regeneration efficiency. With a ε-caprolactone ratio of 55 or less, the reinforcing threads have appropriate hardness that further increases the reinforcing effect, and also have more appropriate decomposition rate, which can reduce calcification.

The threads containing a bioabsorbable material are monofilament threads each having a cross-sectional diameter of 0.1 mm or more and 1 mm or less.

When the threads containing a bioabsorbable material each have a cross-sectional diameter of 0.1 mm or more, the threads can exhibit a higher reinforcing effect, and maintain the bore of the implanted artificial blood vessel against pressure from the surrounding environment to reduce the occurrence of stenosis and clogging. When the threads containing a bioabsorbable material have a cross-sectional diameter of 1 mm or less, the substrate is less likely to harden. In addition, the use of monofilament threads leads to a higher reinforcing effect. The cross-sectional diameter of the threads containing a bioabsorbable material is more preferably 0.20 mm or more, and is more preferably 0.40 mm or less.

The thickness of the threads containing a bioabsorbable material may be expressed in accordance with USP standards for sutures. For example, the thickness may be expressed as 1-0 (cross-sectional diameter of 0.4 to 0.5 mm), 2-0 (cross-sectional diameter of 0.35 to 0.4 mm), or 3-0 (cross-sectional diameter of 0.25 to 0.3 mm).

The inner diameter and length of the artificial blood vessel of the present invention may be selected according to the target blood vessel. The lower limit of the thickness of the artificial blood vessel of the present invention is preferably 50 μm and the upper limit thereof is preferably 5 mm. The artificial blood vessel having a thickness of 50 μm or more can further withstand blood flow and can be easily sutured. The artificial blood vessel having a thickness of 5 mm or less has a more appropriate bioabsorption period, and thus can reduce calcification. The lower limit of the thickness of the artificial blood vessel is more preferably 0.3 mm and the upper limit thereof is more preferably 1.5 mm.

FIG. 2 schematically shows an exemplary structure of the artificial blood vessel of the present invention. In FIG. 2, the reinforcement A is a woven fabric, and the reinforcement B is one shown in FIG. 1(a). The artificial blood vessel of the present invention is a composite in which the reinforcement B 1 and a reinforcement A 2 are positioned inside a foam 3. Such a structure allows the artificial blood vessel to maintain flexibility and cell penetration efficiency derived from the foam 3 while exhibiting high compression resistance derived from the reinforcement B 1 and reinforcement A 2. In addition, the reinforcement B 1 has warp portions 12 as shown in FIG. 1, and thus can reduce expansion and contraction of the artificial blood vessel in the longitudinal direction. This reduces the occurrence of calcification, which can further increase the blood vessel regeneration efficiency.

The artificial blood vessel of the present invention is implanted in an affected area, so that the surrounding cells can penetrate into the artificial blood vessel and proliferate to regenerate a blood vessel. Cells may be seeded onto the artificial blood vessel before use.

The method for producing the artificial blood vessel of the present invention is not limited. For example, the artificial blood vessel may be produced by a method including preparing the reinforcements in advance, placing them in a mold, and pouring into the mold a solution of the bioabsorbable material for forming the foam, followed by freezing and then freeze-drying (freeze-drying method), or a method including preparing the reinforcements in advance, attaching to them a solution of the bioabsorbable material for forming the foam, and then immersing the reinforcements into water to precipitate out the bioabsorbable material (reprecipitation method). In the freeze-drying method, a foam having any of various pore sizes can be prepared by changing the freezing temperature, polymer concentration, and the like. In a dissolution method, the pore size of the foam can be controlled by adjusting the particles of water-soluble substance.

Advantageous Effects of Invention

The present invention can provide an artificial blood vessel that can achieve a balance between cell penetration efficiency and crush resistance and can regenerate a blood vessel at very high efficiency.

DESCRIPTION OF EMBODIMENTS

Embodiments of the present invention are described in more detail with reference to, but not limited to, examples.

(Production of Artificial Blood Vessel)

Figure 1:
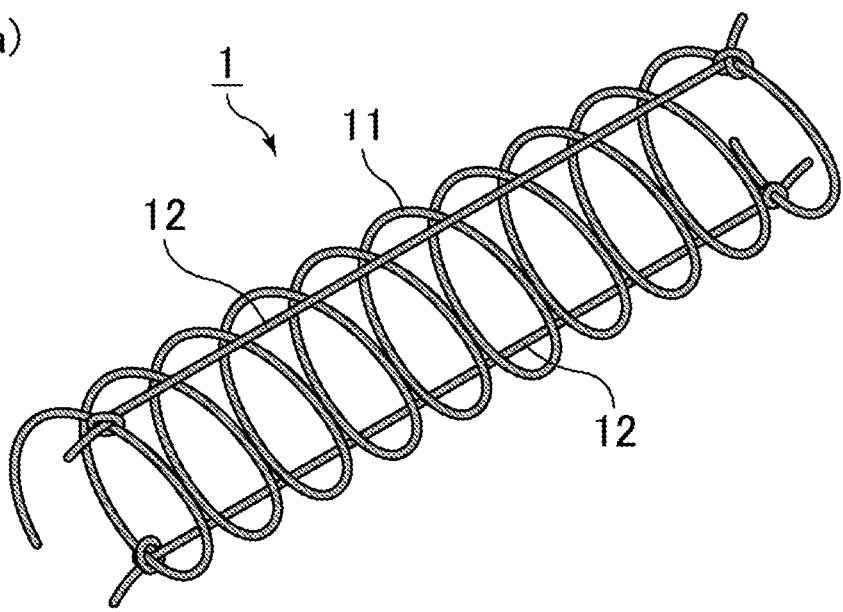
FIG. 1 schematically shows exemplary structures of the reinforcement B in the present invention.
Figure 1:
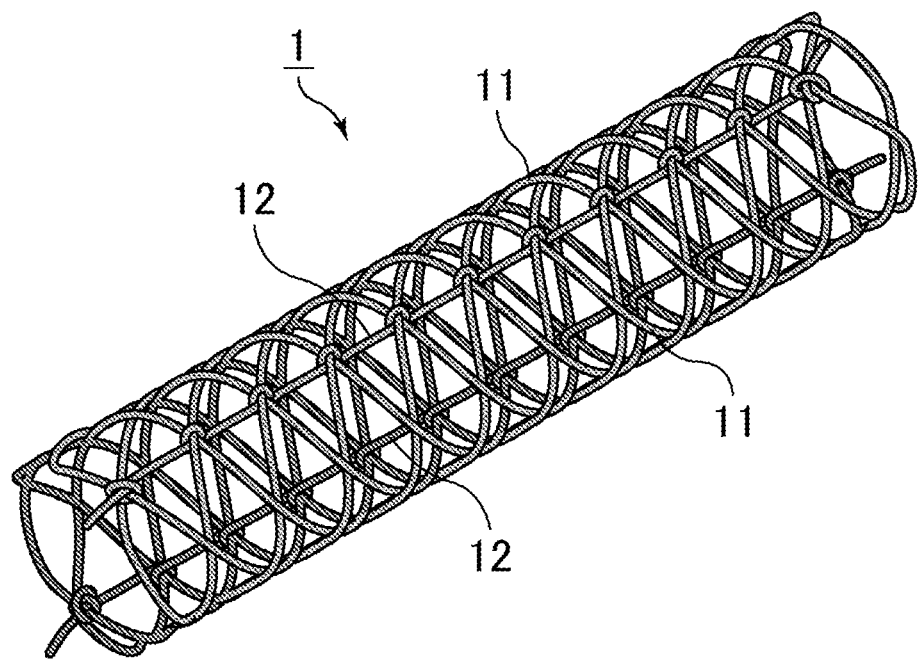
Figure 2:
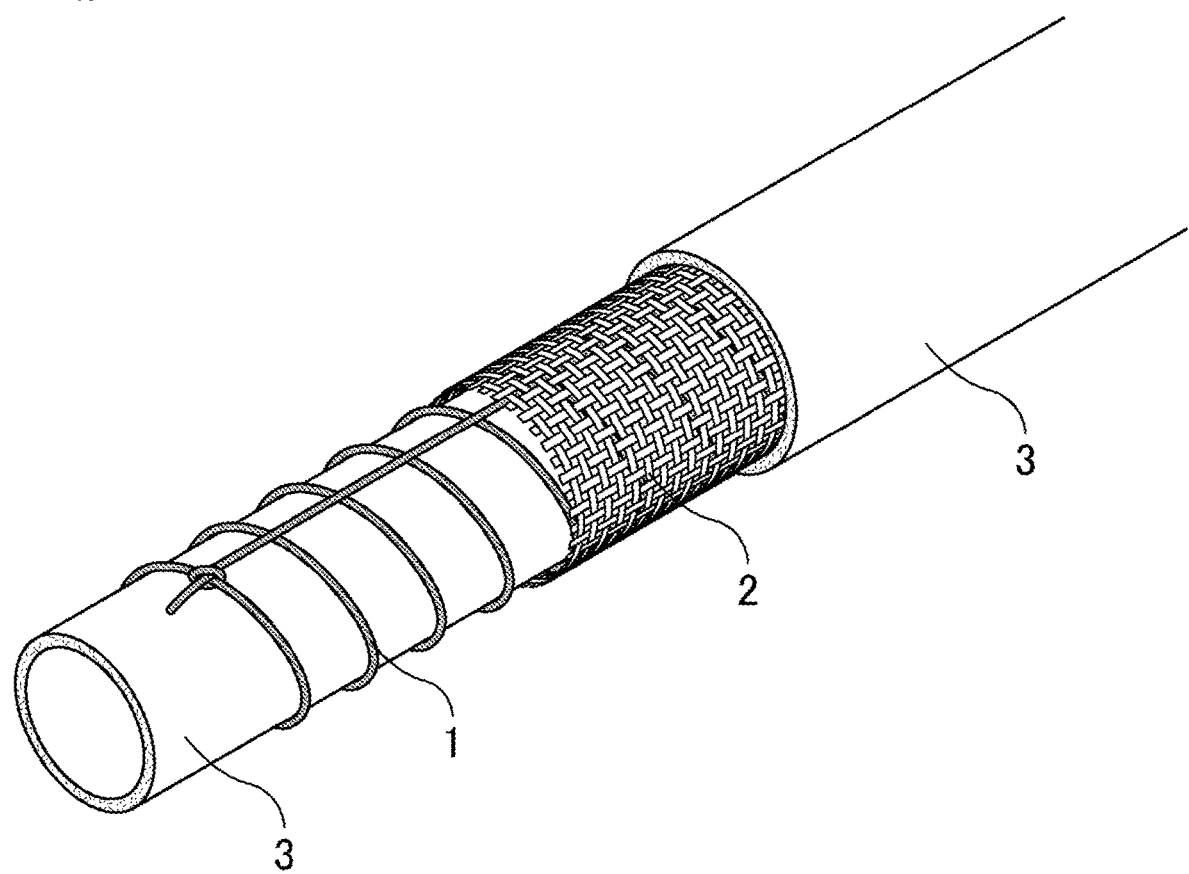
FIG. 2 schematically shows an exemplary structure of the artificial blood vessel of the present invention.

As shown in FIG. 1(b), two monofilament threads (thickness 1-0) of a lactide (D, L, or DL)-ε-caprolactone copolymer were helically wound in opposite directions at a pitch of 3 mm around a Teflon® stick having an outer diameter of 10 mm. Subsequently, as shown in FIG. 1(b), monofilament threads of a lactide (D, L, or DL)-ε-caprolactone copolymer were wrapped once around intersections of the helically wound threads and thus tied, whereby the two longitudinal ends of the winding portion were connected. Thus, a reinforcement B having a winding portion and warp thread portions was obtained. Onto the reinforcement B was attached a tubular, plain-woven fabric made of 140 denier polyglycolic acid thread (reinforcement A).

Subsequently, the Teflon® stick with the reinforcements A and B formed thereon was immersed in a 3.6% by weight solution of a L-lactide-ε-caprolactone copolymer (molar ratio 50:50) in dioxane, and frozen at −80° C. The Teflon® stick was then pulled out, and the resulting hole was filled with a 3.6% by weight solution of a L-lactide-ε-caprolactone copolymer (molar ratio 50:50) in dioxane. Another Teflon® stick having an outer diameter of 9 mm was then inserted, followed by freezing at −80° C. This was followed by freeze-drying at −40° C. to 40° C. for 12 hours, whereby an artificial blood vessel was obtained. The artificial blood vessel was a sandwich-structured composite in which the reinforcements A and B were interposed between foam layers each having a thickness of 1 mm.

INDUSTRIAL APPLICABILITY

The present invention can provide an artificial blood vessel that can achieve a balance between cell penetration efficiency and crush resistance and can regenerate a blood vessel at very high efficiency.

REFERENCE SIGNS LIST

1 reinforcement B
11 winding portion 12 warp thread portion
2 reinforcement A
3 foam

The invention claimed is:

1. An artificial blood vessel having a tubular shape, comprising:
    a foam containing a bioabsorbable material;
    a reinforcement A containing a bioabsorbable material; and
    a reinforcement B including threads containing a bioabsorbable material,
    the foam being reinforced with the reinforcements A and B,
    wherein the reinforcement A is a non-woven fabric, a film, or a weft-knitted, warp-knitted, or woven fabric made of knitted or woven fibers,
    the reinforcement B includes monofilament threads each having a cross-sectional diameter of 0.1 mm or more and 1 mm or less,
    the reinforcement B includes a winding portion having a helical shape, a ring shape, or an X shape and a warp thread portion stretched in a direction parallel to a longitudinal direction of the artificial blood vessel, and
    the artificial blood vessel is a composite including the reinforcement A and reinforcement B inside the foam,
    wherein the winding portion includes a pair of helical threads containing a bioabsorbable material and combined to have opposite winding directions, and
    an intersection of the threads is tied with a thread constituting the warp thread portion.

2. The artificial blood vessel according to claim 1, wherein the threads containing a bioabsorbable material contain at least one selected from the group consisting of poly-L-lactide, a lactide (D, L, or DL)-ε-caprolactone copolymer, and a glycolic acid-ε-caprolactone copolymer.

* * * * *